(12) United States Patent
He et al.

(10) Patent No.: US 8,946,407 B2
(45) Date of Patent: Feb. 3, 2015

(54) FRUCTOSYLATED MANGIFERIN AND PREPARATION METHOD THEREFOR AND USE THEREOF

(75) Inventors: Bingfang He, Nanjing (CN); Xueming Wu, Nanjing (CN); Jianlin Chu, Nanjing (CN); Bin Wu, Nanjing (CN); Sen Zhang, Nanjing (CN); Pingkai Ouyang, Nanjing (CN)

(73) Assignee: Nanjing University of Technology, Nanjing, Jiangsu (CN)

( * ) Notice: Subject to any disclaimer, the term of this patent is extended or adjusted under 35 U.S.C. 154(b) by 0 days.

(21) Appl. No.: 14/001,173

(22) PCT Filed: Mar. 8, 2012

(86) PCT No.: PCT/CN2012/072084
§ 371 (c)(1),
(2), (4) Date: Aug. 23, 2013

(87) PCT Pub. No.: WO2013/004086
PCT Pub. Date: Jan. 10, 2013

(65) Prior Publication Data
US 2014/0221643 A1    Aug. 7, 2014

(30) Foreign Application Priority Data
Jul. 6, 2011    (CN) .......................... 2011 1 0188224

(51) Int. Cl.
*C07H 15/26* (2006.01)
*C12P 19/14* (2006.01)
*C12P 19/00* (2006.01)
*C12P 17/06* (2006.01)

(52) U.S. Cl.
CPC ................ *C07H 15/26* (2013.01); *C12P 19/14* (2013.01); *C12P 19/00* (2013.01); *C12P 17/06* (2013.01)
USPC ........................... 536/123.1; 536/123; 435/99

(58) Field of Classification Search
None
See application file for complete search history.

(56) References Cited

FOREIGN PATENT DOCUMENTS

FR     2882762 A1 *  9/2006

OTHER PUBLICATIONS

Cantagrel, FR 2882762 A1, Sep. 2006, machine translation.*

* cited by examiner

*Primary Examiner* — Layla Bland
(74) *Attorney, Agent, or Firm* — George G. Wang; Bei & Ocean

(57) ABSTRACT

Provided are a fructosylated mangiferin, a preparation method therefor and a use thereof, wherein the fructosylated mangiferin has a structural formula represented by the following formula (I), the method for preparing the fructosylated mangiferin includes adding a substance with fructosylating enzymatic activity to a transformed liquid containing mangiferin for biotransformation reaction, so as to convert the mangiferin into the fructosylated mangiferin, wherein the transformed liquid contains the mangiferin and a glycosyl donor; as well as a use of the fructosylated mangiferin in preparation of a medicament for treatment of tumor-related diseases.

14 Claims, 13 Drawing Sheets

FRUCTOSYLATED MANGIFERIN AND PREPARATION METHOD THEREFOR AND USE THEREOF

CROSS-REFERENCE TO RELATED APPLICATIONS

This application claims priority from CN Application No. 201110188224.6, filed Jul. 6, 2011 and PCT Application No. PCT/CN2012/072084, filed Mar. 8, 2012, the contents of which are incorporated herein in the entirety by reference.

FIELD OF THE INVENTION

This invention is related to a fructosylated mangiferin, a preparation method therefor and a use thereof, in the field of bio-pharmaceutical technology.

BACKGROUND OF THE INVENTION

Mangiferin is a carbon ketoside of tetrahydroxy pyrrones, as a flavonoid compound of xanthone, existing in a variety of plants, such as mango tree, almond tree, gentiana manchurica and rhizome anemarrhenae, and so on. Mangiferin molecular formula: C19H18O11, molecular weight: 422.3. Mangiferin has many biological activity and pharmacologic actions, such as antioxidation, antitumor, immune regulation, anti-glycosuria and anti-inflammation (Deng Jiagang and Xun Lilan, Journal of Changchun University of Traditional Chinese Medicine, 2008, 24(4): 463-464.).

Although with extensive pharmacologic activity, the dissolvability of mangiferin is very low, and this seriously restricts its development as a medical agent, therefore, to facilitate its use, improvement should be made to the dissolvability and bioavailability of mangiferin. Deng Jiagang et al (Deng Jiagang and Yuan Ye, Western China Pharmacy Journal, 2008, 23 (1):17-18.) converted mangiferin 3-phenolic hydroxyl into a phenol sodium salt, and the mangiferin monosodium salt has a mass yield of 92.8%. Mangiferin converted into sodium salt has improved water dissolvability, and can be easily absorbed in gastrointestinal tract, with improved bioavailability and curative effect; experiments have shown that mangiferin and its sodium salt have the function to relieve cough, reduce phlegm and resist inflammation, with good water dissolvability, the monosodium salt of mangiferin has better action than mangiferin, therefore monosodium salt of mangiferin can be expected to develop into a medicine for respiration system. Hu et al (Hu H G, Wang M J, Zhao Q J. Chin Chem Lett, 2007, 18:1323-1326.) obtained a series of 3,6,7-O-trisubstituted mangiferin derivatives after alkylation with mangiferin as raw material, and their structures were all confirmed by H NMR spectroscopy, with compounds 2~11 all being new compounds; preliminary in vitro antidiabetic activity sieving result showed that, at the same concentration, the suppression rate of compounds 5 and 11 to PTPIB doubles that of mangiferin.

For natural active ingredients with complicated structure, structural modification with chemical synthesizing has the disadvantages of low yield, poor reaction specificity and many by-products, especially, some reaction can hardly be realized with chemical means at present, but biological transformation can make up the deficiency of chemical synthesizing. Cantagrel et al (Europe Patent File No.: FR20050002223 20050304; Publishing No.: FR 2882762 (A1)) modified mangiferin by glycosylating the mangiferin with glucosyltransferase originated from two strains of leuconostoc mesenteroides, and obtained glucosyl-β-(1,6)-mangiferin, with mangiferin as glycosyl receptor and cane sugar as glycosyl donor (CASRN:908570-23-0). With Leuconostoc mesenteroides NRRL B-1299 strains as biocatalyst, under the condition of 0.4 g/L mangiferin and 40 g/L cane sugar, the yield in glycosylating reaction is 25%; with Leuconostoc mesenteroides NRRL 521-F strains as biocatalyst, under the condition of 0.4 g/L mangiferin and 40 g/L cane sugar, the yield in glycosylating reaction is 28%.

After glycosylation of mangiferin, its water dissolvability is substantially improved, but till today, no relevant research report has been available on whether the change in molecular structure after glycosylating modification will affect the pharmacological activity of mangiferin. Due to the low water dissolvability of mangiferin, in glycosylating modification of mangiferin with biotransformation method, the mangiferin concentration before transformation is generally low (not exceeding 0.5 g/L), and the mole transformation rate of product is also low (not exceeding 30%), and such restrictions have made it quite difficult to obtain sufficient product for pharmacological experiments on tumor-related diseases and the subsequent industrialized production.

SUMMARY OF THE INVENTION

Therefore, an object of this invention is to provide a fructosylated mangiferin for the treatment or tumor-related diseases with good therapeutic effect with respect to the existing deficiency that the mangiferin concentration is generally low before glycosylating reaction and transformation, and the mole transformation rate of product is also low, unable to obtain a sufficient amount of product for the treatment of tumor-related diseases.

Another purpose of this invention is to provide the preparation method of the said fructosylated mangiferin.

A more object of this invention is to provide the use of said fructosylated mangiferin in preparing medicine for the treatment of tumor-related diseases.

For the above objects, the technical plan of this invention is as follows:

In one respect, this invention provides a fructosylated mangiferin, the fructosylated mangiferin has the structure as shown in formula (I) below:

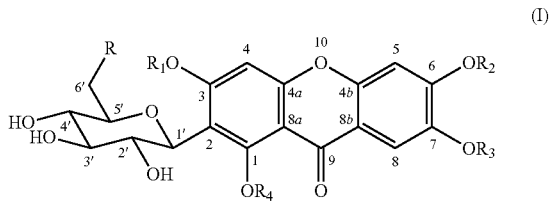

Where $R_1$, $R_2$, $R_3$ and $R_4$ are selected respectively as one of the hydrogen, methyl, ethyl, formoxyl, acetyl, methylamino and acidophobe; R is a monoglysosyl of fructose or an oligosaccharyl of 2 fructose molecules linked together, in the structure as shown in formula (II):

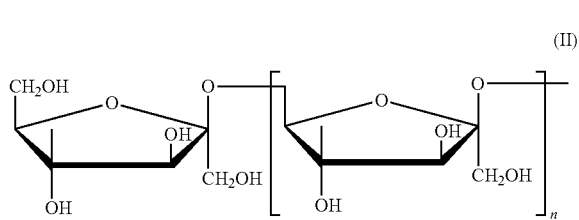
(II)

Where n=0–1.

In another respect of the invention, it provides a preparation method for fructosylated mangiferin, which includes adding a substance with fructosylating enzymatic activity into a transformed liquid containing mangiferin for biotransformation reaction, so as to convert the mangiferin into the fructosylated mangiferin, wherein the transformed liquid contains the mangiferin and a glycosyl donor, preferably, the said glycosyl donor is fructose or cane sugar.

Preferably, the said method also includes removing the bacteria cells or bacteria protein from the transformed liquid after the completion of transformation reaction, purifying it with resin and then obtain fructosylated mangiferin powder or crystal from the resin-purified fructosylated mangiferin fraction by drying it with rotary evaporation or freezing.

Preferably, the said substance with fructosylating enzymatic activity includes fermentation liquor with fructosylating enzymatic activity, the fermentation liquor supernatant, purified fructosylating enzyme and fructosylating enzyme recombined expression protein.

Preferably, the said fructosylating enzyme is β-D-fructofuranosidase.

More preferably, the said β-D-fructofuranosidase is originated from bacteria of *Arthrobacter* sp., with a molecular weight of about 60 kDa, and the first 5 amino acid sequences at the N end being respectively ATEPV.

Preferably, the said fermentation liquor or fermentation liquor supernatant is obtained by fermenting microorganisms with fructosylating enzymatic activity.

Preferably, the said microorganism is *Arthrobacter nicotianae*, its collection No. is CCTCC M2010164 (scientific name in Latin: *Arthrobacter nicotianae* XM6, classification nomenclature: *Arthrobacter nicotianae* XM6, collection No.: CCTCC No.: M2010164, preserved at China Typical Culture Collection Center on Jun. 29,2010, address: Wuhan University, Wuhan, China, Zip: 430072).

Preferably, the fermentation of the said microorganism was conducted with fermentation medium containing: cane sugar of 5~80 g/L, peptone of 5~50 g/L, $KH_2PO_4$ 0.4~4 g/L, $CaCl_2$ 0.5~5 g/L, $MnSO_4$ 0.1~2 g/L, pH 6-8, which is put in a shake flask at 25~40° C., and oscillating at 10~400 rpm, or in a fermenting tank for agitating with ventilation, at a speed and ventilatory capacity of 1~6 vvm, 10~400 rpm, to ferment for 6~48 hours.

Preferably, the fermentation of the said microorganism was conducted with fermentation medium containing cane sugar of 15 g/L, peptone of 25 g/L, $KH_2PO_4$ 2 g/L, $CaCl_2$ 2 g/L, $MnSO_4$ 0.2 g/L, pH 7.5, which is put in a shake flask at 30° C., and oscillating at 240 rpm for 16 hours, or in a fermenting tank for agitating with ventilation, at a speed and ventilatory capacity of 4 vvm, 300 rpm, to ferment for 6 hours. Preferably, the transformation reaction of the said microorganism took place in a nonaqueous phase condition.

Preferably, the said nonaqueous phase reaction condition is: oscillating in a shake flask at 10~400 rpm or agitating in a fermenting tank, in 5~50% hydrophilic organic solvent, with mangiferin concentration of 0.1~70 g/L, the mangiferin to glycosyl donor at a mole ratio 1:1~1:200, and added with 10%~50% fermentation liquor or fermentation liquor supernatant, the said fermentation liquor or fermentation liquor supernatant containing fructosylated enzyme 10~100 U/mL, and the reaction lasted 6~400 hours at 25~40° C., in a buffer solution of pH4~8.

More preferably, the said hydrophilic organic solvent is one or several selected from dimentyl sulfoxide (DMSO), dimentyl formamide (DMF), acetonitrile, methanol, acetone or ethanol.

Preferably, the said nonaqueous phase reaction condition is: a solution with 20% of DMSO, 62.7 g/L of mangiferin and 200 g/L of cane sugar as glycosyl donor, added with 20% of fermentation liquor supernatant, the said fermentation liquor supernatant containing fructosylating enzyme at 30 U/mL, and it was put into a 5 L fermenting tank containing phosphate buffer at 1/15 mol/L and pH6.86, for transformation with agitation at 300 rpm at 30° C. for 360 hours.

Preferably, the said resin purification is passing the transformed liquid containing fructosylated mangiferin through AB-8 macroporous resin for adsorption; after the adsorption, the remaining glycosyl donor is washed off with eluant, followed by gradient or stage elution with the eluant, to obtain the fructosylated mangiferin.

Preferably, distilled water with pH 4~4.5 in a quantity 10 times the column bed volume is used to remove the remaining glycosyl donor, then methanol or ethanol solution at 5~30% is used for gradient or stage elution, to obtain fructosylated mangiferin.

Preferably, in the transformation reaction under nonaqueous phase reaction condition, this adsorption should be conducted under the condition that the organic solvent in the transformed liquid has been removed by evaporation at low temperature or has been diluted to less than 2% volumetric ratio.

Preferably, the said method also includes elution and recovery of remaining mangiferin with the eluant.

Preferably, 100% methanol or ethanol is used to elute and recover the remaining mangiferin.

On the other hand, this invention provides the use of the fructosylated mangiferin in preparing medicine for the treatment of tumor-related diseases.

Moreover, this invention provides a fructosylated mangiferin mentioned in this invention for the treatment of tumor-related diseases.

Furthermore, this invention provides a method to treat tumor-related diseases, including giving the subjects with the said fructosylated mangiferin in this invention at a dosage effective for the treatment, and preferably, the said subjects being mammal, and the said mammal being preferably human being.

As compared with existing technologies, the beneficial effects of this invention are:

First, the inventor has invented a new fructosylated mangiferin, and experiments have proved that this new type mangiferin derivative has substantial suppression effect in vitro on human chronic myelogenous leukemia cell strain K562, so it can be used to treat tumor-related diseases, and this has enriched the fructosylated derivatives of mangiferin as sources of medicine, but for existing fructosylated derivatives of mangiferin, no report on pharmacological activity has been seen.

Second, as compared with mangiferin, this new type fructosylated mangiferin has better dissolvability, making up a defect of mangiferin product, increasing the safety in medicine application and improving therapeutic effect therefore it is a new drug product with good prospects of development.

Furthermore, the inventor has provided the biotransformation of this new type fructosylated mangiferin. When existing biotransformation methods are used in glycosylating modification of mangiferin, due to the low water dissolvability of mangiferin, the mangiferin concentration before transformation is generally low (not exceeding 0.5 g/L), and the mole transformation rate of product is also low (not exceeding 30%), while with the biotransformation method in this invention, in the 20% DMSO transformation system, with 62.7 g/L mangiferin as transformation substrate, the concentration of monofructosyl-β-(2,6)-mangiferin obtained can be 63.0 g/L, and the transformation rate of fructosylated mangiferin is 87%, thus solving the technical difficulty with existing technologies, conducive to using this product in pharmacological tests for tumor-related diseases and subsequent industrial production.

BRIEF DESCRIPTION OF DRAWINGS

In the following, the embodiments of this invention are described in detail with drawings, in which.

BIOLOGICAL MATERIAL COLLECTION INFORMATION

Figure 1:
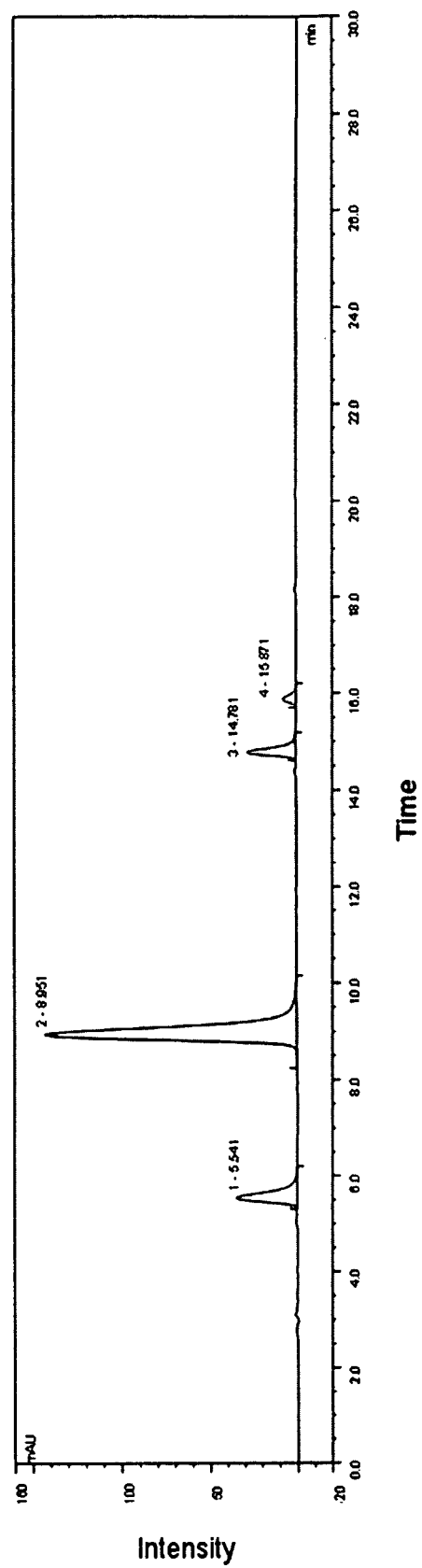
FIG. 1 shows the HPLC spectrum of nonaqueous phase biotransformed mangiferin.

Latin name: *Arthrobacter nicotianae* XM6, classified name: *Arthrobacter nicotianae* XM6, depositary No.: CCTCC No.: M2010164, preserved at China Typical Culture Collection Center on Jun. 29, 2010, address: Wuhan University, Wuhan, China, Zip: 430072.

DETAILED DESCRIPTION OF PARTICULAR EMBODIMENTS OF THE INVENTION

It is understood that, the specific implementation methods described here are presented in the form of specific embodiments, which do not constitute restrictions to this invention. Without deviating from the scope of this invention, the main features of this invention can be used in various embodiments. Technical personnel in this field will be aware or can confirm that by merely using conventional experiments, many equivalents can be applied in specific steps described herein. Such equivalents are believed as within the scope of this invention, and be covered by the claims.

In the following embodiments, processes and methods not described in detail are generally known conventional methods in this field. The sources and trade names of the reagents used and their components necessarily to be listed are indicated when first appeared, and all identical reagents used subsequently are identical to those indicated first unless specially noted.

Embodiment 1 Obtaining Fructosylated Mangiferin by Nonaqeuous Biotransformation of Mangiferin Put 40 mL of culture medium 2 cultured by fermentation (the culture medium composition as shown in Table 2) into a 250 mL trianglar flask, after sterilization with high pressure steam at 121° C. for 20 min, inoculate the *Arthrobacter nicotianae* XM6 (CCTCC M2010164), ferment and culture it by oscillating at 30° C. and 180 rpm for 16 hours, and inoculate as seed liquor into a 5 L fermentation tank, at an amount of 5 volumetric percentage, the fermentation tank is loaded with 3 L of liquid, and is sterilized in the same way as the shake flask. It is fermented and cultured at 30° C. and 300 rpm, with ventilation rate of 3 vvm, for 6 hours (with OD at about 10), then it is centrifuged at 8000 rpm for 20 min, the supernatant enzyme liquor is collected, to determine that the supernatant enzyme liquor contains fructosylating enzyme of 30 U/mL. For this, the following method is adopted in determining the enzyme activity:

Preparation of substrate solution: 0.01 g mangiferin and 1 g cane sugar are fully dissolved in 100 mL of 1/15 mol/L phosphate buffer (pH6.86). Reaction system: take 2 mL of 1/15 mol/L phosphate buffer (pH6.86) and add it into 18 mL of substrate solution, and let it react at 30° C. for 10 min, then immediately take out 100 μL and add it into 900 μL of methanol to terminate the reaction, as a blank control. Meanwhile take 2 mL of enzyme liquor and add it into 18 mL of substrate solution, and let it react at 30° C. for 10 min, then immediately take out 100 μL and add it into 900 μL of methanol to terminate the reaction, as a sample. Then determination is performed with HPLC. The enzyme activity unit is defined as: the amount of enzyme required to transform 1 μmol of mangiferin at 30° C. is one activity unit (1 U is 1 μmol/min). Definition of specific activity (U/mL): the enzyme activity (U) number in unit volume (mL) of enzyme liquor.

Add 600 mL of supernatant enzyme liquor into a 5 L fermenting tank with total volume of 3000 mL of 1/15 mol/L phosphate buffer (pH6.86) containing 62.7 g/L of mangiferin (purchased from Nanjing Zelang Medical Science and Technology Co., Ltd.), 200 g/L of cane sugar, for mangiferin glycosylating reaction at 30° C. and 300 rpm, after 360 hours, heat it for 2 hours at 45° C. to terminate the transformation reaction. The transformed liquid is determined with HPLC as: containing monofructosyl-β-(2,6)-mangiferin of 63.0 g/L, and bifructosyl-β-(2,6)-mangiferin of 15.7 g/L, so the fructosylated mangiferin transformation rate is as high as 87%. As shown in FIG. 1, it is mangiferin with a retaining time of 14.781 min, monofructosyl-β-(2,6)-mangiferin with a retaining time of 8.951 min and bifructosyl-β-(2,6)-mangiferin with a retaining time of 5.541 min.

The said transformed liquid containing fructosylated mangiferin is absorbed with AB-8 macroporous resin (with a chromatographic column of 40×600 mm, at a flow rate of 10 mL/min), then the remaining glycosyl donor is washed off with pH4~4.5 distilled water (the pH regulated with glacial acetic acid) at a volume 10 times the column bed volume, followed by gradient elution with 5%-30% methanol solution, to obtain fructosylated mangiferin (with purity >97%), and finally the pigment and mangiferin are washed off with 100% methanol.

The fructosylated mangiferin with purity >97% is dried by rotary evaporation at 45° C. or freezing, to obtain monofructosyl-β-(2,6)-mangiferin powder or crystal of 158.5 g, and bifructosyl-β-(2,6)-mangiferin powder or crystal of 39.1 g.

As determined, at 25° C., the dissolvability of monofructosyl-β-(2,6)-mangiferin is 350 g/L, and that of bifructosyl-β-(2,6)-mangiferin is 1200 g/L, respectively 3.5×103 times and 1.2×104 times that of mangiferin (0.1 g/L) under the same condition.

Figure 2:
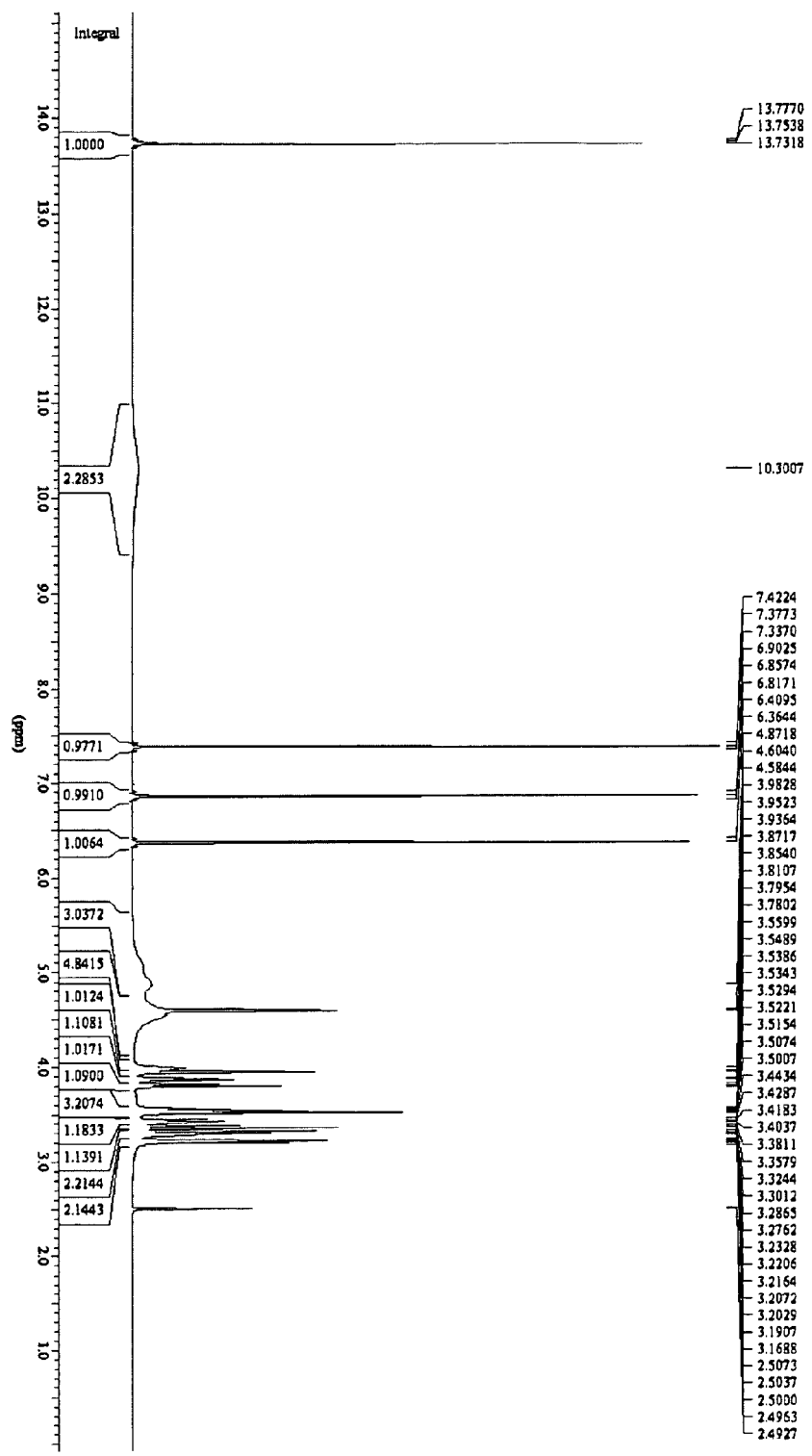
FIG. 2 shows the $^1$HNMR spectrum of monofructosyl-β-(2,6)-mangiferin.
Figure 4:
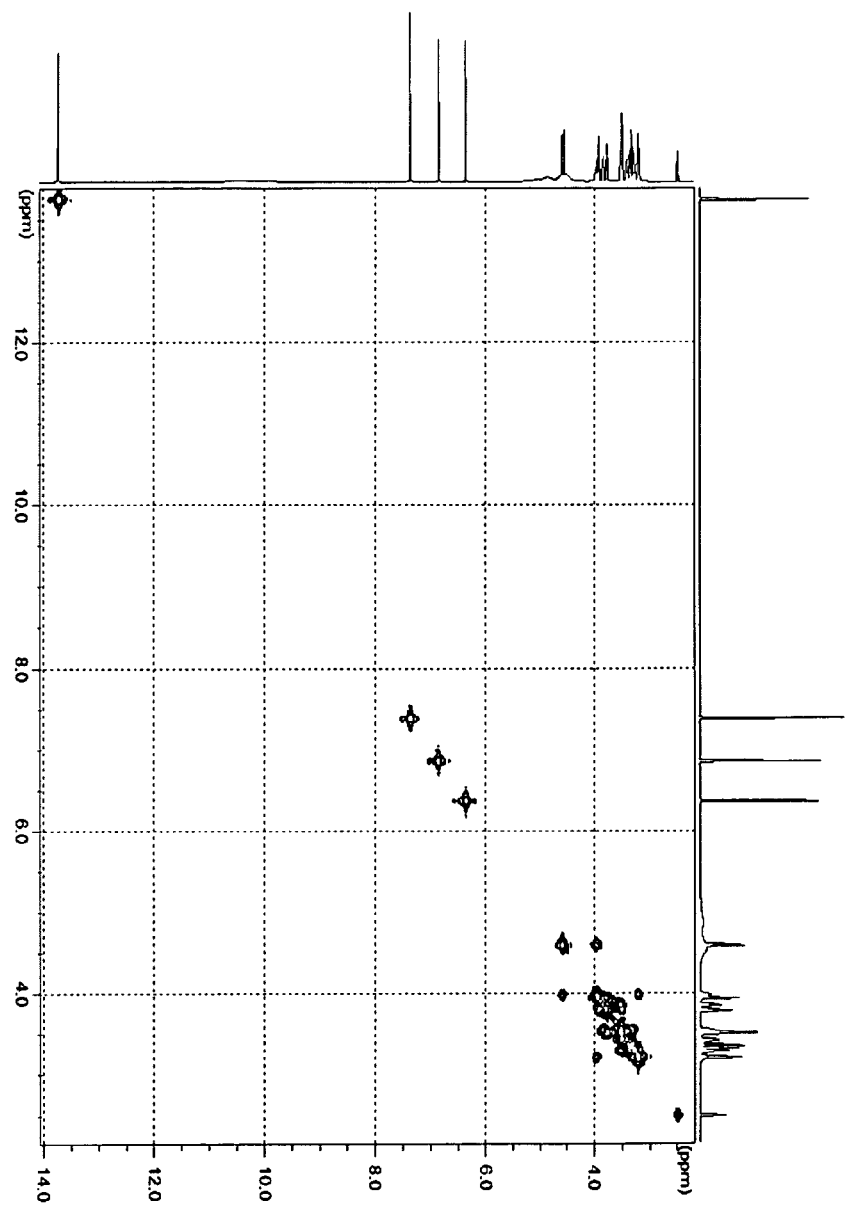
FIG. 4 shows the H—H COSY spectrum of monofructosyl-β-(2,6)-mangiferin.
Figure 5:
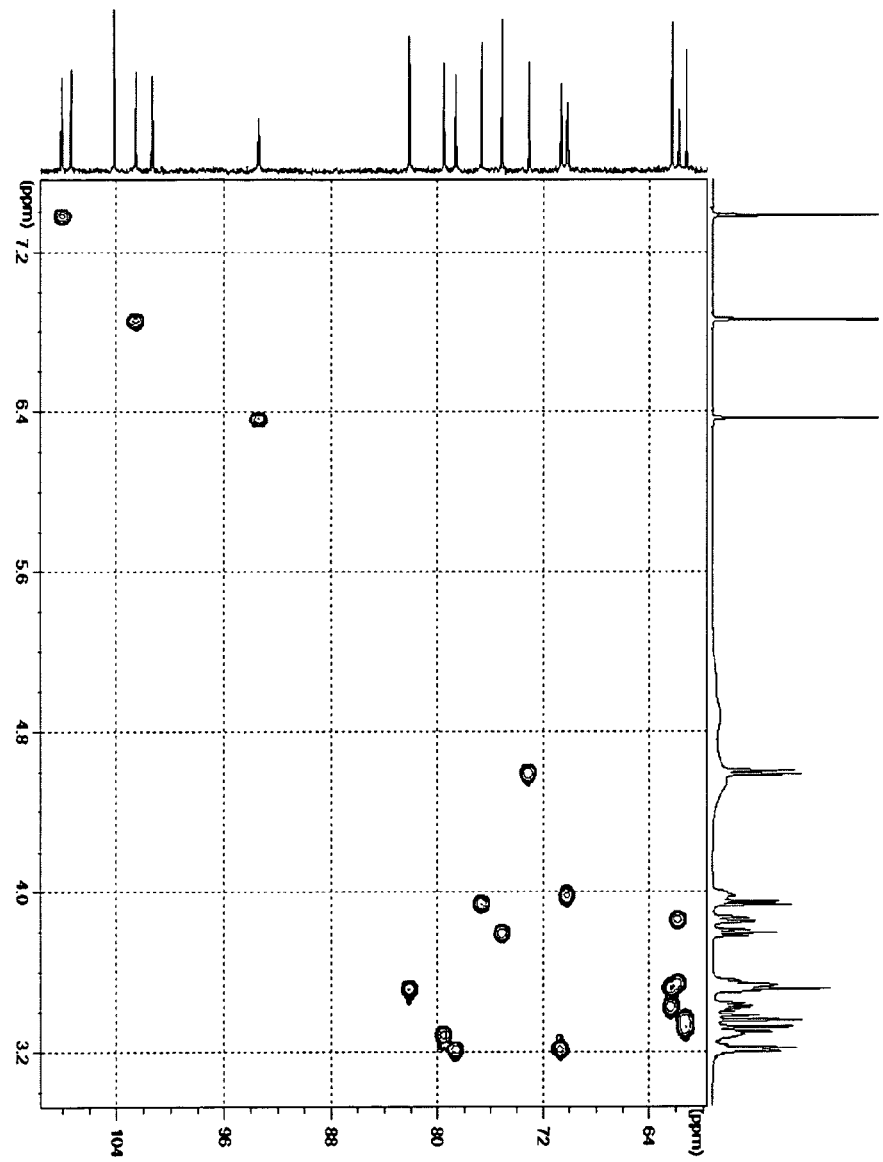
FIG. 5 shows the C—H HSQC spectrum of monofructosyl-β-(2,6)-mangiferin.
Figure 6:
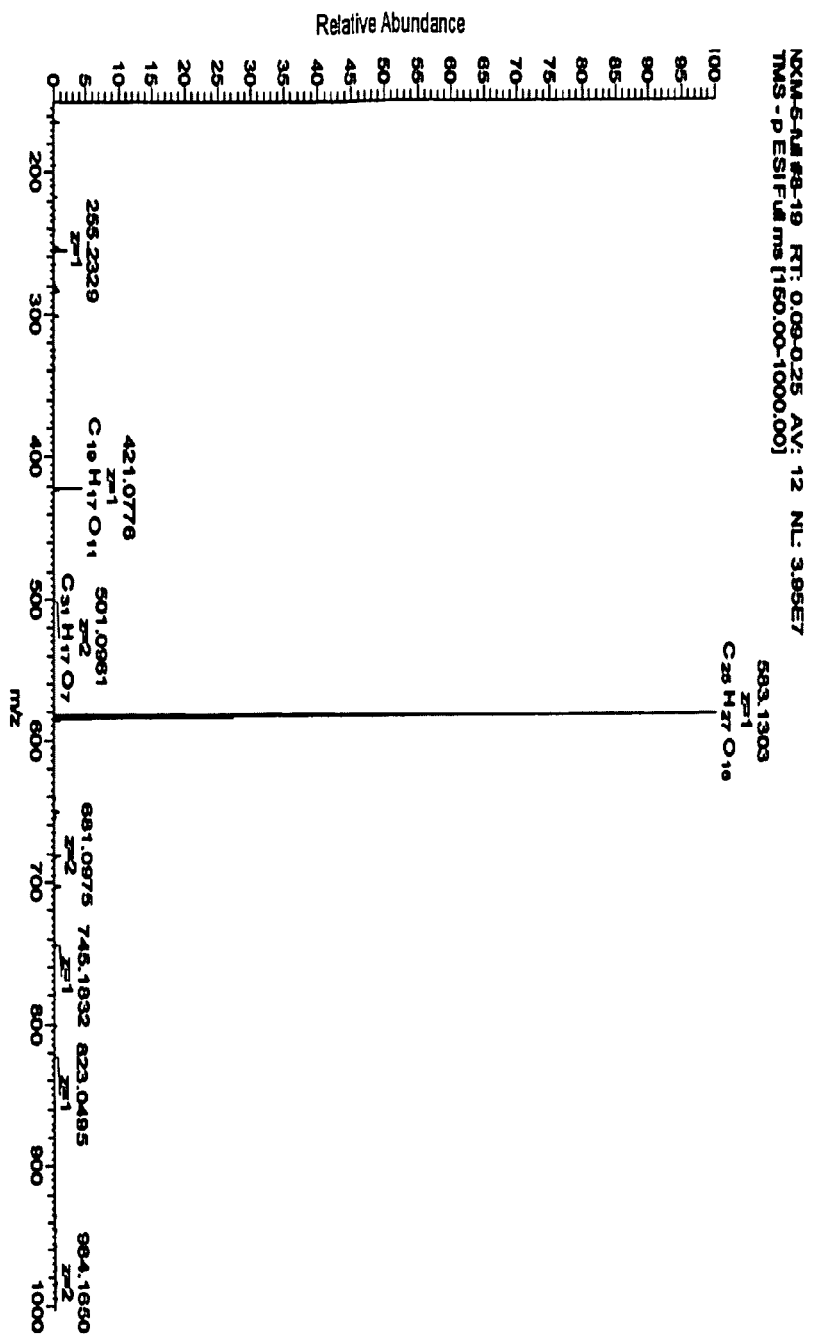
FIG. 6 shows the high resolution mass spectrum of monofructosyl-β-(2,6)-mangiferin.

The said monofructosyl-β-(2,6)-mangiferin: HR-MS: m/z 583.1303[M-H]-, element composition is $C_{25}H_{27}O_{16}$ (FIG. 6), M-H calculated value 583.1299; the 1H-NMR and 13C-NMR chemical displacement features in DMSO are respectively as follows:

1H-NMR(500 MHz, DMSO-d6) δ: 13.75(1H, s, 1-OH), 7.38(1H, s, H-8), 6.86(1H, s, H-5), 6.36(1H, s, H-4), 4.59(1H, d, J=9.8 Hz, H-1'), 3.92-4.00(2H, m, H-2'/H-4"), 3.77-3.89 (2H, m, H-5'/H-6"), 3.50-3.56(3H, m, H-5", H-6', H-6"), 3.20-3.42(7H, m, H-2", H-3', H-4', H-6', 2H-1", H-3") (FIG. 2, FIG. 4, FIG. 5).

Figure 3:
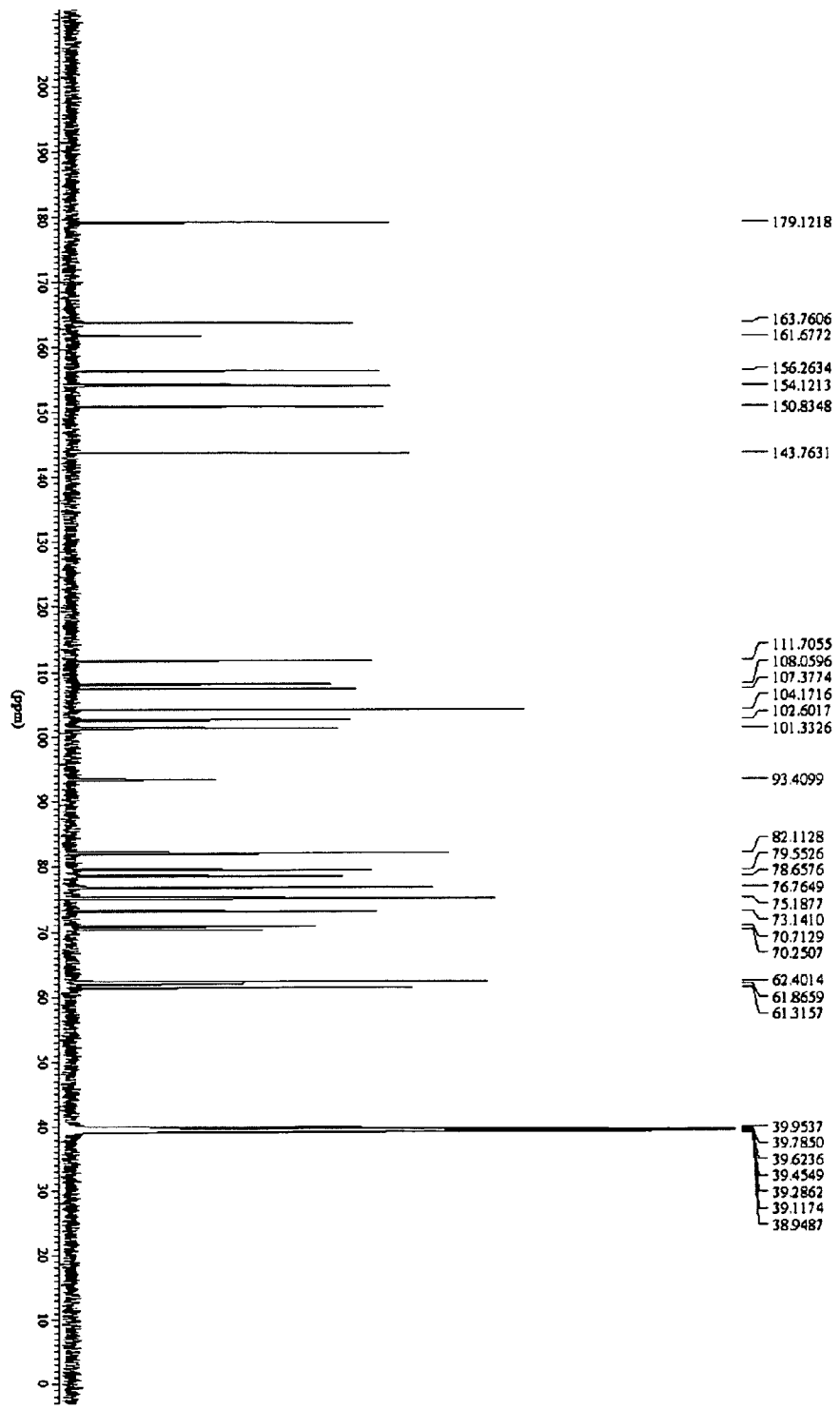
FIG. 3 shows the $^{13}$CNMR spectrum of monofructosyl-β-(2,6)-mangiferin.

13C-NMR(500 MHz, DMSO-d6) δ: 179.1, 163.8, 161.7, 156.3, 154.1, 150.8, 143.7, 111.7, 108.1, 107.4, 104.2(C-2"), 102.6, 101.3, 93.4, 82.1(C-5"), 79.6, 78.7, 76.7, 75.2(C-5'), 73.1, 70.7, 70.2, 62.4(C-6'), 61.9(C-6"), 61.3(FIG. 3).

Figure 7:
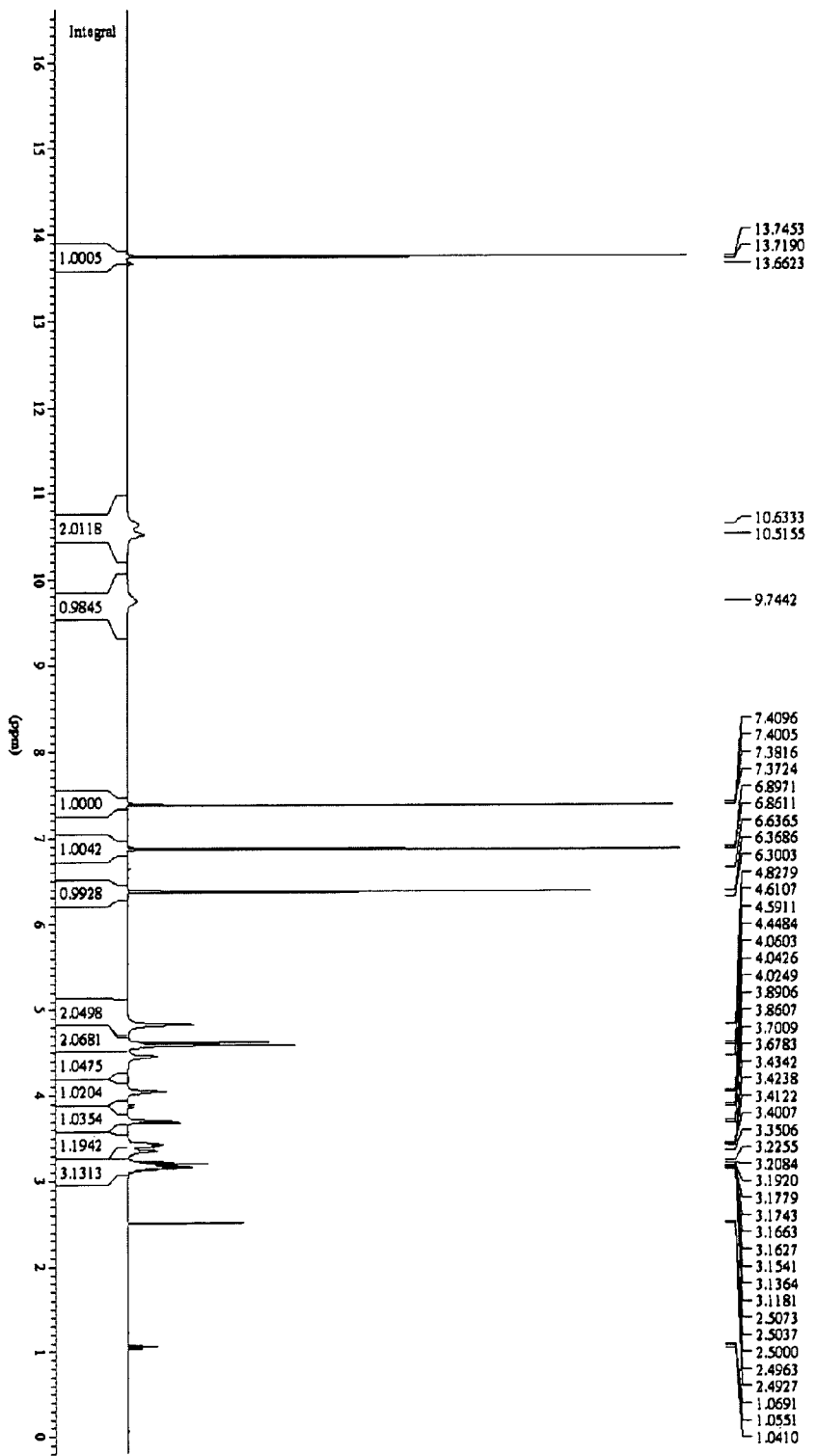
FIG. 7 shows the $^1$HNMR spectrum of mangiferin.

The 1H-NMR and 13C-NMR chemical displacement features in DMSO of mangiferin are respectively as follows:

1H-NMR (500 MHz, DMSO-d6) δ: 13.75(1H, s, 1-OH), 10.63(1H, s, 6-OH), 10.52(1H, s, 3-OH), 9.74 (1H, s, 7-OH), 7.38 (1H, s, H-8), 6.86 (1H, s, H-5), 6.37(1H, s, H-4), 4.60 (1H, d, J=9.8 Hz, H-1'), 4.04(1H, m, H-2'), 3.42, 3.70(2H, m, H-6'), 3.12-3.23(3H, m, H-3', H-4', H-5') (FIG. 7).

Figure 8:
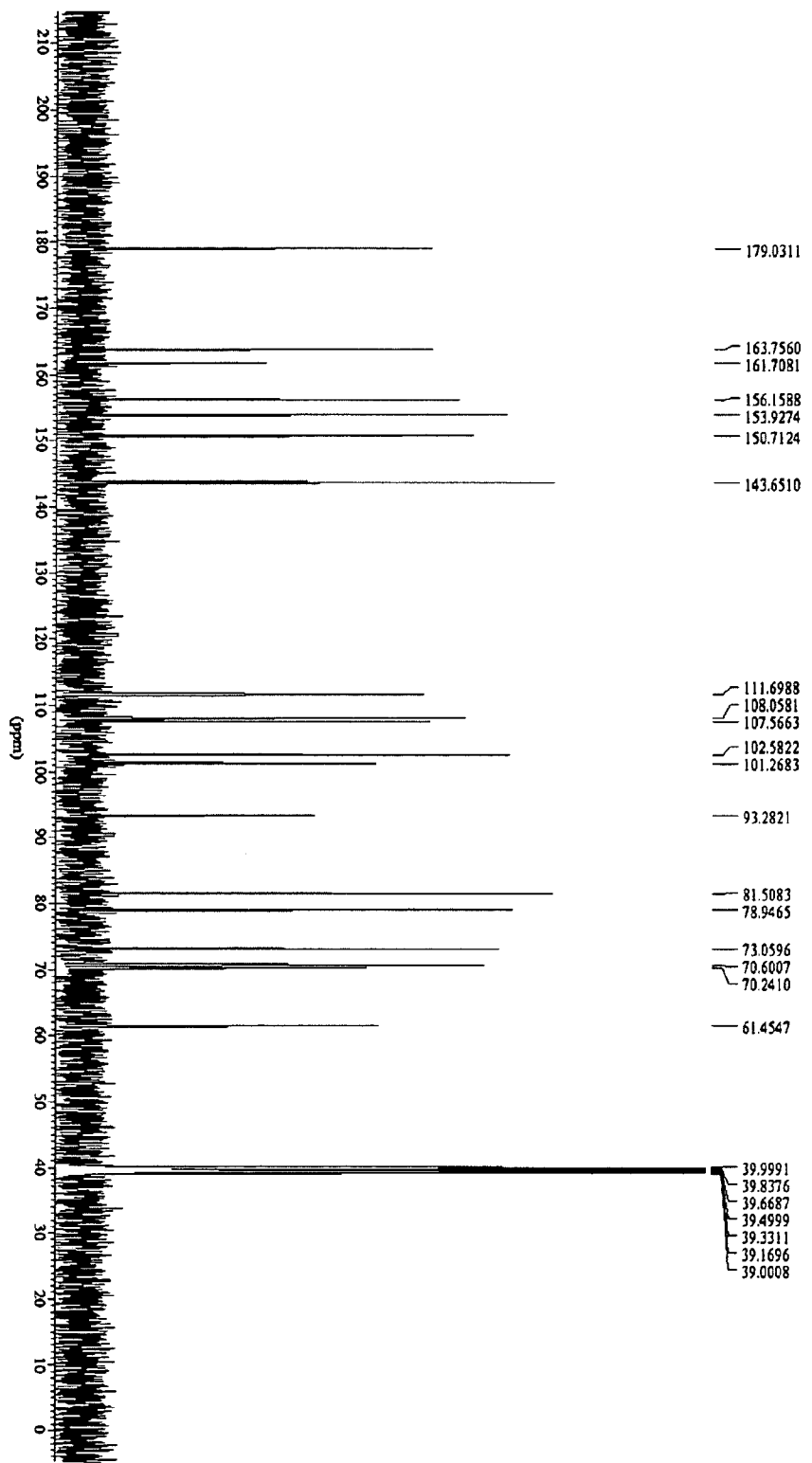
FIG. 8 shows the $^{13}$CNMR spectrum of mangiferin.

13C-NMR(500 MHz, DMSO-d6) δ: 179.0, 163.8, 161.7, 156.2, 153.9, 150.7, 143.7, 111.7, 108.1, 107.6, 102.6, 101.3, 93.3, 81.5(C-5'), 78.9, 73.1, 70.6, 70.2, 61.5(C-6')(FIG. 8).

Figure 13:
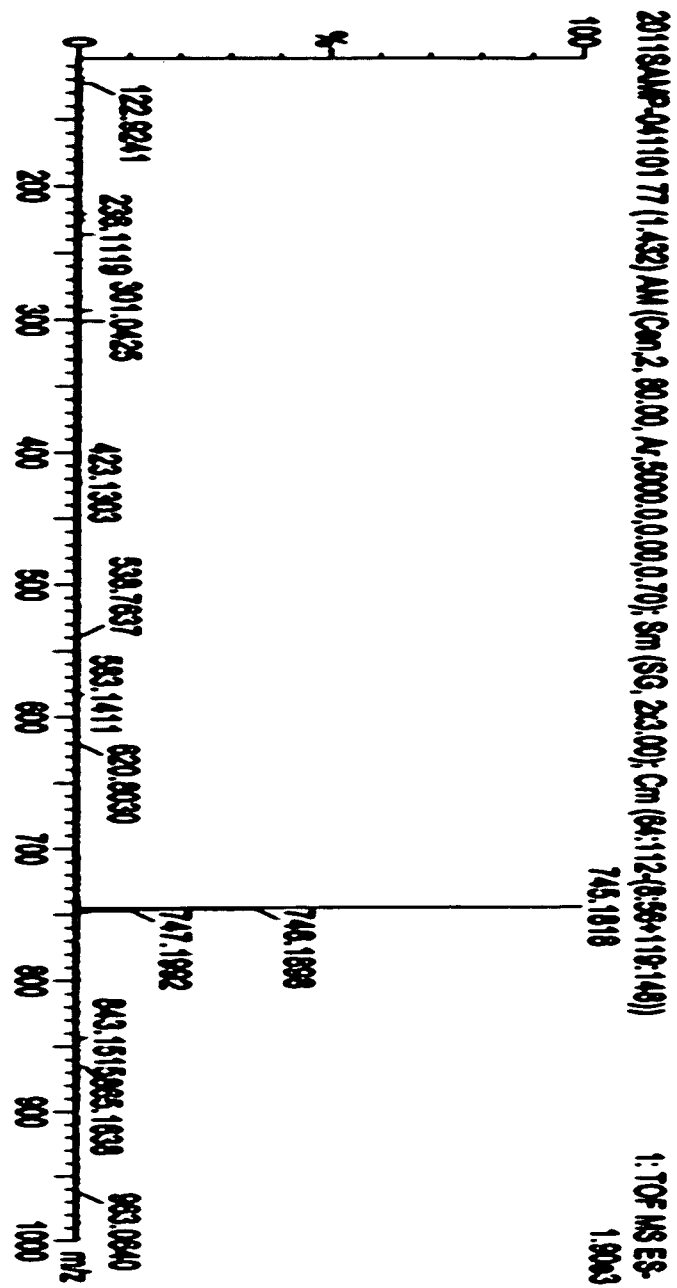
FIG. 13 shows the high resolution mass spectrum of bifructosyl-β-(2,6)-mangiferin.

Single mass analysis is performed for bifructosyl-β-(2,6)-mangiferin, as shown in FIG. 13, HR-MS: Deviation=20.0 PPM/DBE: min=−1.5, max=20.0, without selecting filter, single element and even electricion mass spectrum, and the elements used are C: 0-50, H:0-100, 0:0-50, calculation is performed in the limited four results (Table 1) (each element has nearly 30 close results) to obtain formula 202, m/z 745.1818[M-H]-, the element composition is $C_{31}H_{37}O_{21}$, and M-H calculated value 745.1827;

TABLE 1

Limited four results used to calculate formulas

| Mass | Calculated mass | mPa | PPM | DBE | i-FIT | Formula |
|---|---|---|---|---|---|---|
| 745.1818 | 745.1827 | −0.9 | −1.2 | 13.5 | 0.2 | $C_{31}H_{37}O_{21}$ |
| | 745.1886 | −6.9 | −9.1 | 4.5 | 11.8 | $C_{24}H_{41}O_{26}$ |
| | 745.1734 | 8.4 | 11.3 | 0.5 | 32.5 | $C_{20}H_{41}O_{29}$ |
| | 745.1675 | 14.3 | 19.2 | 9.5 | 7.0 | $C_{27}H_{37}O_{24}$ |

Figure 9:
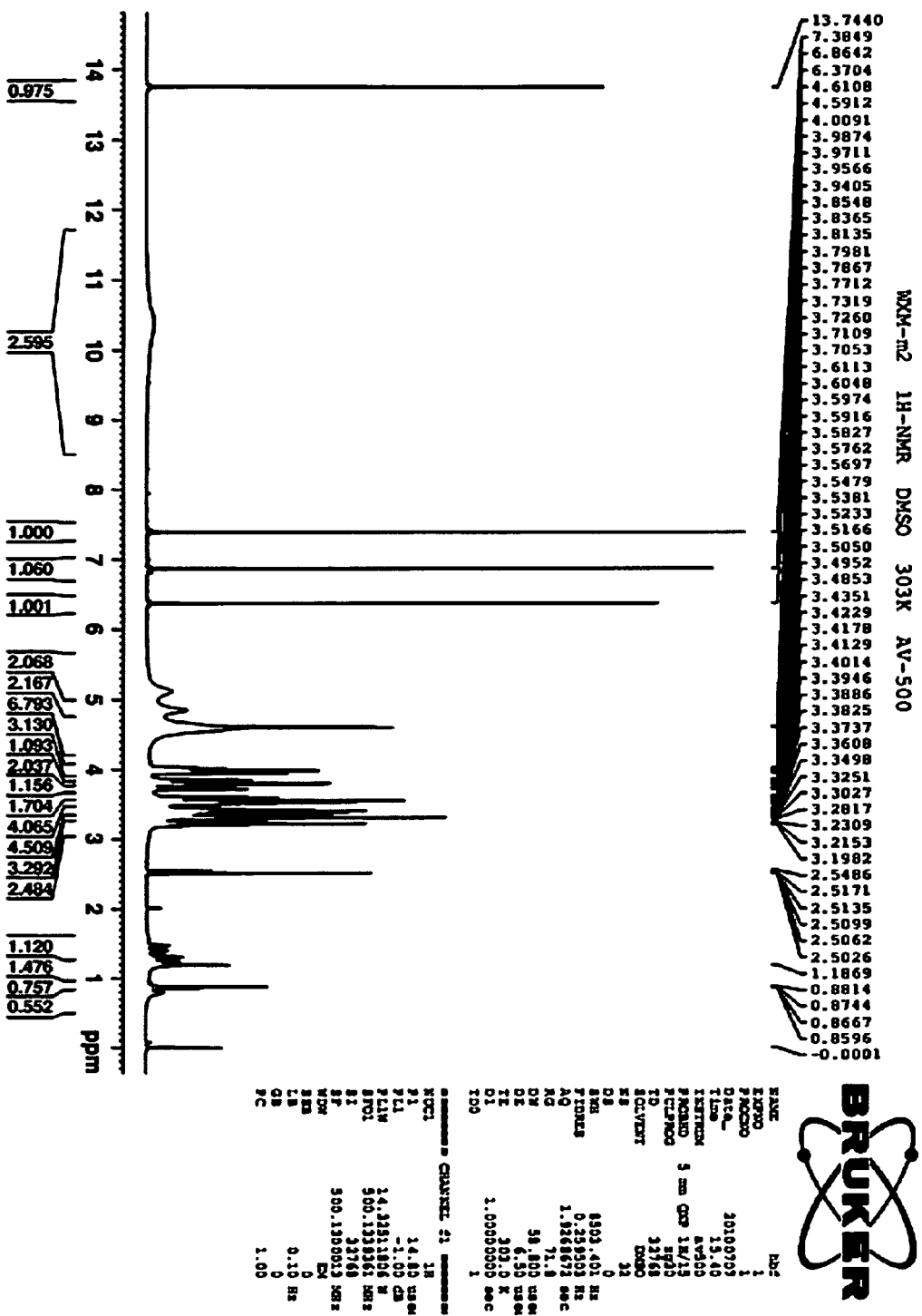
FIG. 9 shows the $^1$HNMR spectrum of bifructosyl-β-(2,6)-mangiferin.
Figure 11:
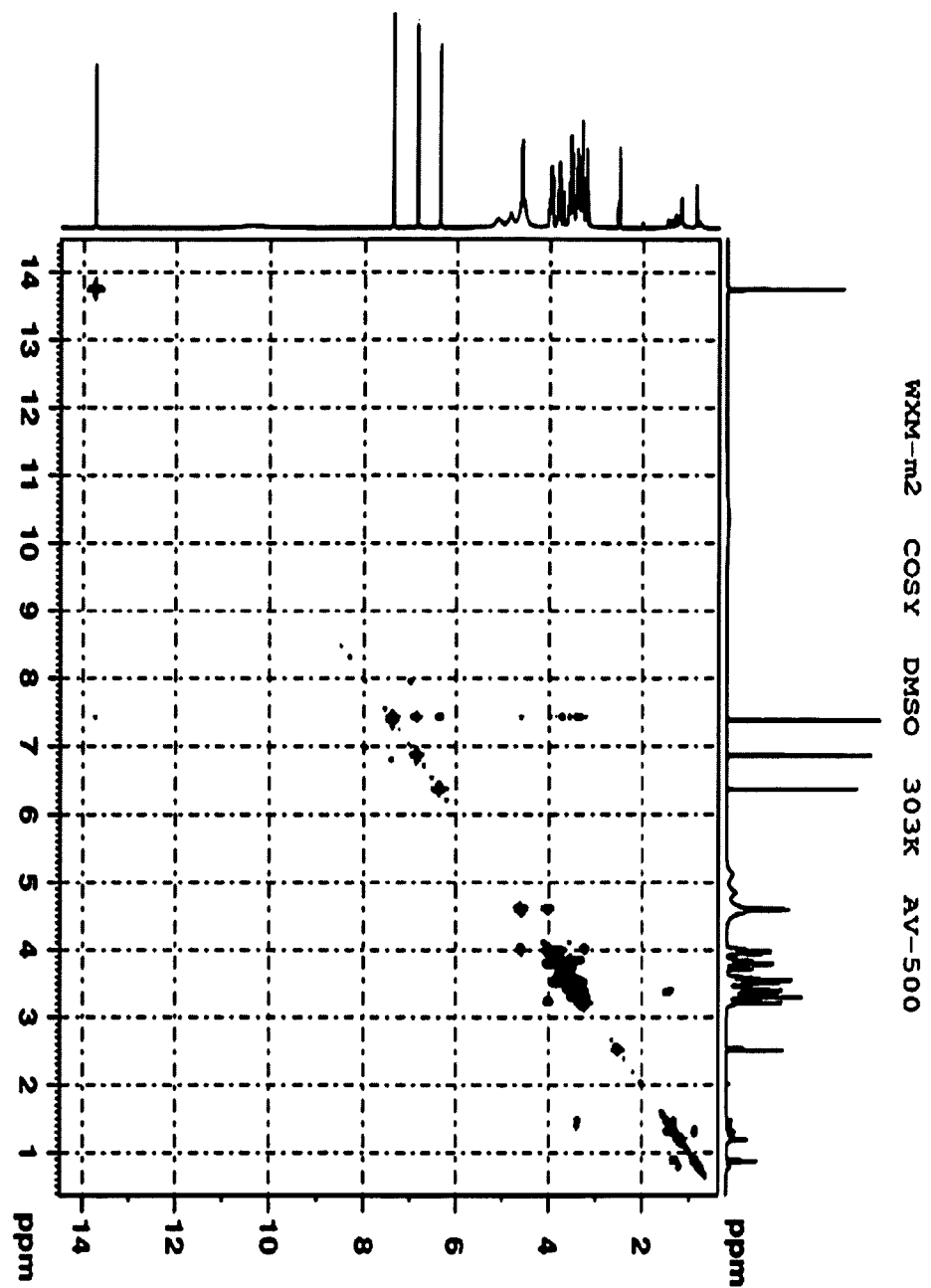
FIG. 11 shows the H—H COSY spectrum of bifructosyl-β-(2,6)-mangiferin.
Figure 12:
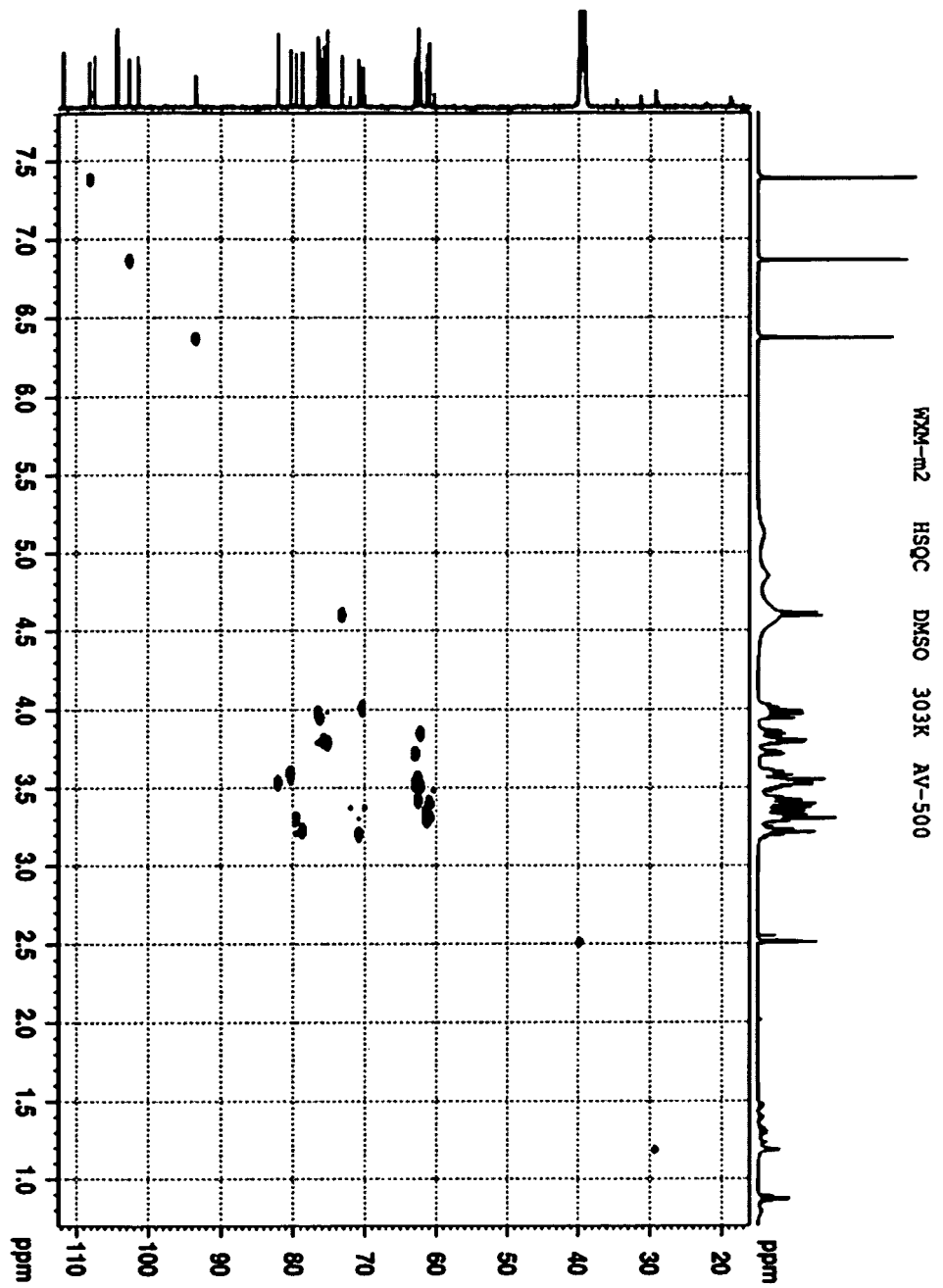
FIG. 12 shows the C—H HSQC spectrum of bifructosyl-β-(2,6)-mangiferin.

The 1H-NMR and 13C-NMR chemical displacement features in DMSO are respectively as follows:

1H-NMR(500 MHz, DMSO-d6) δ: 13.75(1H, s, 1-OH), 7.38(1H, s, H-8), 6.86(1H, s, H-5), 6.37(1H, s, H-4), 4.60(1H, d, J=9.8 Hz, H-1'), 3.94-4.02(3H, m, H-2', H-4", H-4'''), 3.71-3.85(4H, m, H-5', H-6', H-5", H-6"), 3.48-3.61(5H, m, H-6', H-3", H-6", H-5''', H-6'''), 3.18-3.43(9H, m, H-3', H-4', 2H-1", H-3", H-6", 2H-1''', H-3''') (FIG. 9, FIG. 11 and FIG. 12).

Figure 10:
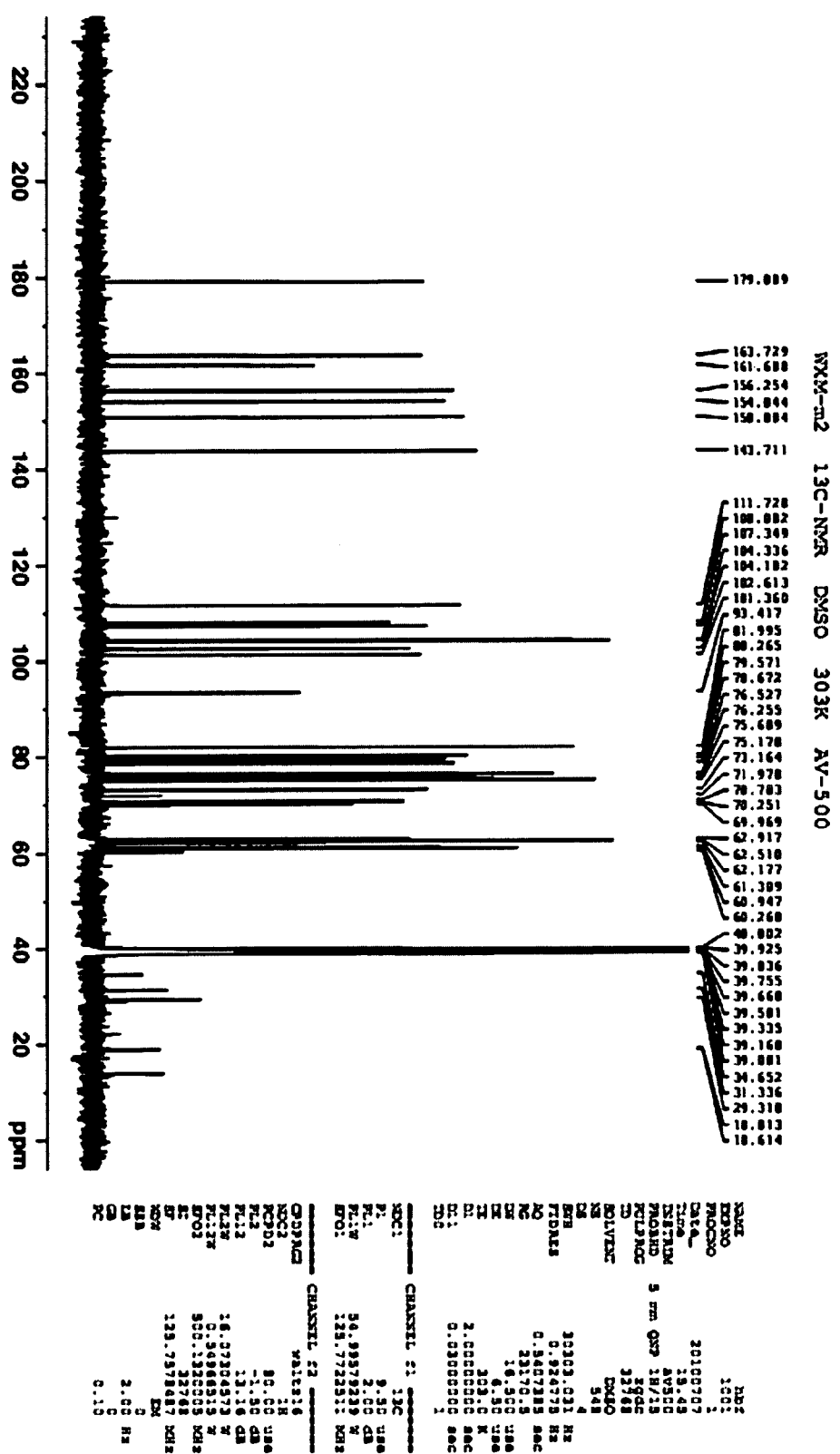
FIG. 10 shows the $^{13}$CNMR spectrum of bifructosyl-β-(2,6)-mangiferin.

13C-NMR(500 MHz, DMSO-d6) δ: 179.1, 163.7, 161.7, 156.3, 154.1, 150.8, 143.7, 111.7, 108.1, 107.3, 104.3(C-2"), 104.2(C-2''), 102.6, 101.4, 93.4, 80.3, 82.0(C-5"), 79.6, 78.3, 76.5, 76.3, 75.7(C-5"), 75.2(C-5'), 73.2, 70.8, 70.3, 62.9(C-6'), 62.5(C-6"), 62.2(C-6"), 61.3, 60.9 (FIG. 10).

Embodiment 2 Obtaining Fructosylated Mangiferin by Nonaqeuous Biotransformation of Mangiferin Put 40 mL of culture medium 2 cultured by fermentation (the culture medium composition as shown in Table 2) into a 250 mL trianglar flask, after sterilization with high pressure steam at 121° C. for 20 min, inoculate the *Arthrobacter nicotianae* XM6 (CCTCC M2010164), ferment and culture it by oscillating at 30° C. and 180 rpm for 6 hours (with OD at about 10), then it is centrifuged at 8000 rpm for 20 min, the supernatant enzyme liquor is collected, to determine that the supernatant enzyme liquor contains fructosylating enzyme of 30 U/mL.

Move 4 mL of supernatant into a 250 mL triangular flask with plug with a total of 20 mL phosphate buffer (pH6.86) containing 20.9 g/L mangiferin, 200 g/L cane sugar and 20% DMSO, for transformation with oscillation at 30° C. and 180 rpm, and after 96 hours, heat it for 2 hours at 45° C. to terminate the transformation reaction. The transformed liquid is determined with HPLC as: containing monofructosyl-β-(2,6)-mangiferin of 21.9 g/L, and bifructosyl-β-(2,6)-mangiferin of 8.2 g/L, so the fructosylated mangiferin transformation rate is as high as 97.8%.

The said transformed liquid containing fructosylated mangiferin is diluted 10 times and absorbed with AB-8 macroporous resin (with a chromatographic column of 40×600 mm, at a flow rate of 10 mL/min), then the remaining glycosyl donor is washed off with pH4~4.5 distilled water (the pH regulated with glacial acetic acid) at times the column bed volume, followed by gradient elution with 5%-30% methanol solution, to obtain fructosylated mangiferin (with purity >97%), and finally the pigment and mangiferin are washed off with 100% methanol. The fructosylated mangiferin with purity >97% is rotary evaporated at 45° C. or frozen dried, to obtain monofructosyl-β-(2,6)-mangiferin powder or crystal of 0.364 g, and bifructosyl-β-(2,6)-mangiferin powder or crystal of 0.136 g.

Embodiment 3 Effect of Different Fermentation and Transformation Conditions on Formation of Products Put 40 mL of culture medium cultured by fermentation (the culture medium composition as shown in Table 2) into a 250 mL trianglar flask, after sterilization with high pressure steam at 121° C. for 20 min, inoculate the *Arthrobacter nicotianae* XM6 (CCTCC M2010164), and ferment and culture it by oscillating under different fermenting conditions (refer to Table 2 for fermenting conditions), then it is centrifuged at 8000 rpm for 20 min, the supernatant enzyme liquor is collected, to determine that the supernatant enzyme liquor contains fructosylating enzyme of 10-100 U/mL. Add 20% supernatant enzyme liquor into the transformation system, after oscillating transformation under different transformation conditions (refer to Table 3 for transformation conditions), heat it for 2 hours at 45° C. to terminate the transformation reaction, and the transformed liquid is determined with HPLC.

Different culture fermentation conditions and transformation conditions produce different effect on the formation of fructosylated mangiferin product, Tables 2 and 3 show the changes in mole transformation rate of the main products monofructosylated mangiferin and bifructosylated mangiferin in mangiferin glycosylating reaction under different conditions.

TABLE 2

Different proportions of culture components

| Culture medium composition | Cane sugar (g/L) | peptone (g/L) | $KH_2PO_4$ (g/L) | $CaCl_2$ (g/L) | $MnSO_4$ (g/L) | PH |
|---|---|---|---|---|---|---|
| 1 | 5  | 5  | 0.4 | 0.5 | 0.1 | 6 |
| 2 | 35 | 25 | 2   | 2   | 0.5 | 7 |
| 3 | 80 | 50 | 4   | 5   | 2   | 8 |
| 4 | 5  | 25 | 2   | 2   | 0.5 | 7 |
| 5 | 35 | 50 | 0.4 | 0.5 | 0.1 | 6 |
| 6 | 80 | 5  | 4   | 5   | 2   | 8 |

TABLE 3

Mole transformation rate of monofructosyl-β-(2,6)-mangiferin (M1) and bifructosyl-β-(2,6)-mangiferin (M2) under different conditions

| Ferm. time (h) | Ferm. temp. (° C.) | Medium comp. | Conv. time (h) | Conv. temp. (° C.) | Conv. scale (mL) | Substrate concentration (g/L) | Molar ratio of substrate and cane sugar | Solvent | Solvent prop. (%) | M1 (%) | M2 (%) |
|---|---|---|---|---|---|---|---|---|---|---|---|
| 6  | 25 | 1 | 6   | 25 | 20   | 0.1 | 1:1  | DMF         | 10 | 60 | 10 |
| 12 | 30 | 2 | 12  | 30 | 300  | 5   | 1:5  | Methanol    | 20 | 84 | 3  |
| 18 | 40 | 3 | 400 | 35 | 3000 | 70  | 1:10 | DMSO        | 40 | 45 | 0  |
| 36 | 30 | 4 | 24  | 25 | 20   | 0.1 | 1:1  | Acetone     | 50 | 0  | 0  |
| 12 | 25 | 5 | 204 | 30 | 3000 | 50  | 1:10 | DMSO        | 20 | 74 | 16 |
| 48 | 40 | 6 | 48  | 40 | 500  | 5   | 1:5  | Acetonitril | 20 | 20 | 0  |
| 6  | 30 | 6 | 36  | 25 | 500  | 5   | 1:5  | Ethanol     | 20 | 30 | 0  |
| 12 | 40 | 2 | 36  | 30 | 3000 | 30  | 1:10 | DMSO        | 30 | 40 | 5  |
| 24 | 25 | 3 | 24  | 40 | 20   | 10  | 1:1  | Methanol    | 30 | 45 | 0  |
| 8  | 40 | 1 | 180 | 30 | 3000 | 40  | 1:8  | DMSO        | 20 | 74 | 18 |
| 12 | 30 | 5 | 6   | 30 | 20   | 0.1 | 1:1  | Acetone     | 10 | 48 | 5  |
| 18 | 25 | 1 | 24  | 40 | 200  | 0.5 | 1:10 | Methanol    | 10 | 0  | 0  |
| 6  | 40 | 3 | 400 | 25 | 3000 | 5   | 1:10 | Methanol    | 40 | 10 | 0  |
| 12 | 25 | 2 | 24  | 30 | 500  | 70  | 1:5  | DMSO        | 50 | 5  | 0  |
| 48 | 30 | 1 | 240 | 40 | 20   | 0.1 | 1:1  | DMF         | 40 | 0  | 0  |

It can be seen from the results in Table 3 that, the advantage of nonaqueous phase transformation lies in that the mangiferin concentration in the transformation system can be raised to 70 g/L. Under the preferable nonaqueous phase transformation conditions, the transformation rate can be as high as 87%, the concentration of transformed product is substantially increased (with 62.7 g/L mangiferin, the total transformed product can be 78.7 g/L), and the transformed products can be regulated and controlled by selection and proportion of solvent. These advantages of nonaqueous phase transformation are conducive to industrial production.

Embodiment 4 Experiment on Suppression Effect of monofructosyl-β-(2,6)-mangiferin on Tumor Cell Proliferation 1. Cell Strain and Drug Human chronic myelogenous leukemia cell strain K562, purchased from the cell bank of Shanghai Cell Research Institute of Chinese Academy of Sciences; mangiferin, purchased from Nanjing Zelang Medical Science and Technology Co., Ltd.; monofructosyl-β (2,6)-mangiferin is prepared with the method described in this invention, with purity over 99% as determined by high performance liquid chromatography.

2. Preparation of Experimental Drug and Solution

Drug liquid and its storage: weigh 8.44 mg mangiferin powder and dissolve it in 2 mL DMSO to prepare it into 10 mmol/L mangiferin; weigh 11.68 mg monofructosyl-β (2,6)-mangiferin powder and dissolve it in 2 mL DMSO to prepare it into 10 mmol/L monofructosyl-β (2,6)-mangiferin; they are filtered with a 0.22 μm filter, packed in 1000 μL/doff and stored at −20° C., meanwhile, high concentration DMSO is filtered with a 0.22 μm filter for use as control.

Cell culture liquor: take 1 pack of RPM 1-1640 culture medium (powder) and dissolve it into 800 mL triple-distilled water, agitate it with a magnetic agitator for at least half an hour to complete dissolution, add 2 g of $NaHCO_3$, after sufficient dissolution, bring it to a constant volume of 1 L. Filter it with a filtration membrane of 0.22 pm pore size to remove bacteria, add the serum to a final serum concentration of 10%, and store it at 4° C.

PBS phosphate buffer: dissolve in 800 mL of distilled water 8 g NaCl, 0.2 g KCL, 1.44 g $Na_2PO_4$ and 0.24 g $KH_2PO_4$, regulate the pH of the solution to 7.4 with HCl, add water to a constant volume of 1 L, sterilize it with high pressure steam for 20 min. and store it a low temperature.

MTT application liquid: weight 500 mg MTT powder, dissolve it in 100 mL PBS, after dissolving it with agitation, filter it with a filtration membrane of 0.22 pm pore size to remove bacteria, separate it and stored it at a dark place at 4° C. for later use.

Triple liquid: take SDS 25 g, isopropanol 12.5 mL and concentrated HCl 2.5 mL and add triple distilled water to a constant volume of 1 L, and store it at low temperature.

3. Main Reagents and Instruments

HPLC instrument (DIONEX model: P600); ELISA instrument (Molecular Devices Company Model: spectra MAX 190/GEMINIXS); CO2 incubator (Forma Company Model: 3111); low speed centrifuge (Thermostat Model: PICO-17); inverted microscope (Leica Company Model: DMIL); horizontal rockers (Nanjing University Instruments Company Model: TY-80S); calf serum (Gibaco BRL Company); RPMI1640 (US Gibco Company); Penicillin G Sodium Salt (AMRESCO Company); Streptomycin Sulfate (AMRESCO Company); Trypsin (AMRESCO Company); and MTT (AM-RESCO Company).

4. Cell Culture

The K-562 cells are cultured in RPMI-1640 complete culture medium containing inactivated calf serum at volume fraction of 10%, 100 U penicillin and streptomycin, in an incubating box at 37° C., with 5% CO2 and at saturated humidity.

5. Experimental Method
5.1 K562 Cell Toxicity Test

Take K-562 cells in logarithmic growing phase, adjust its concentration to 1×105/mL, and inoculate them in a 96-hole culture plate, each hole with 90 μL of suspended cell liquid, the experimental group is treated with mangiferin and monofructosyl-β (2,6)-mangiferin at different end concentration (1, 5, 10, 20, 50, 100, 150 and 200 μmol/L), with 10 μL in each hole, the DMSO solvent control group is added with 20 μL PBS containing the corresponding drug solvent, and the blank group is added with 20 μL PBS. For each drug concentration, 6 repeating holes are provided. The culture plate is put back into the cell culture box, add 20 μL MTT (5 mg/mL) solution after 48 h, and after further incubation of 4 h in the culture box, add triple liquid 100 μL into each hole, put it still overnight to allow full dissolution of crystal. Vibrate it with oscillator for 20 min and determine the light absorption at 490 nm with a fully automatic ELISA instrument, and calculate the average suppression rate, the suppression rate (%)=(control group A490−test group A490)/control group A490), the experiment was repeated three times.

6. Statistic Processing

Relevant analysis and Student t tests in Microsoft Excel 2003 were used, and data are presented in.

7. Experimental Results
7.1 Effect of Mangiferin Derivative on Proliferation of Human Chronmyelogenors Leukemia Cell Strain K562

TABLE 4

Effect of mangiferin and monofructosyl-β(2,6)-mangiferin in different concentration on K562 cell proliferation after acting for 48 h

| Group | Mangiferin | | Monofructosyl-β(2,6)-mangiferin | |
|---|---|---|---|---|
|  | OD value | Average suppression rate (%) | OD value | Average suppression rate (%) |
| Control group | 1.032 ± 0.072 |  | 1.029 ± 0.026 |  |
| 1 μmol/L group | 0.952 ± 0.034* | 7.74 | 0.982 ± 0.039* | 4.53 |
| 5 μmol/L group | 0.945 ± 0.041* | 8.39 | 0.938 ± 0.102 | 8.79 |
| 10 μmol/L group | 0.921 ± 0.036* | 10.75 | 0.944 ± 0.053** | 8.19 |
| 20 μmol/L group | 0.995 ± 0.086 | 3.52 | 0.941 ± 0.040** | 8.56 |
| 50 μmol/L group | 1.096 ± 0.143 | −3.9 | 0.938 ± 0.041** | 8.87 |
| 100 μmol/L group | 1.198 ± 0.048** | −16.08 | 0.790 ± 0.098** | 23.19 |
| 150 μmol/L group | 1.141 ± 0.049 | −10.61 | 0.653 ± 0.026*** | 36.53 |
| 200 μmol/L group | 1.182 ± 0.175* | −14.56 | 0.602 ± 0.021*** | 41.48 |

Note:
Compared with control group, *P <0.05, P <0.01, *P <0.001.

Note: Compared with control group, *P<0.05, P<0.01, *p<0.001.

The statistic results after analysis with MTT method show that (see Table 4), both mangiferin and monofructosyl-β (2,6)-mangiferin can substantially reduce the number of K562 cells after acting for 48 h. As compared with the control group during the same time period, there is substantial difference with low dosage of monofructosyl-β (2,6)-mangiferin at 1 μmol/L (P<0.05), and this difference becomes extremely apparent (P<0.001) when the dosage reaches 150 and 200 μmol/L, the suppression rate of K562 cell is respectively 36.53% and 41.48%, indicating that monofructosyl-β (2,6)-mangiferin can markedly suppress the proliferation of human chronmyelogenors leukemia cell strain K562, its suppression effect on K562 cell is substantially higher than that of mangiferin, and the suppression rate increases with the increase of dosage.

While there have been described and pointed out fundamental novel features of the invention as applied to a preferred embodiment thereof, it will be understood that various omissions and substitutions and changes, in the form and details of the embodiments illustrated, may be made by those skilled in the art without departing from the spirit of the invention. The invention is not limited by the embodiments described above which are presented as examples only but can be modified in various ways within the scope of protection defined by the appended patent claims.

What is claimed is:

1. A fructosylated mangiferin, comprising a structure of formula (I):

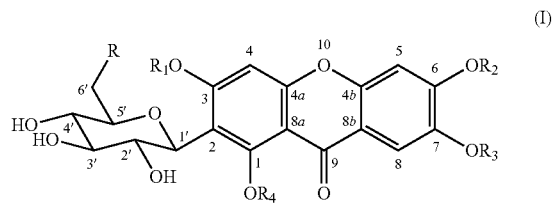

wherein $R_1$, $R_2$, $R_3$ and $R_4$ are each independently selected from the group consisting of hydrogen, methyl, ethyl, formoxyl, acetyl, methylamino and acidophobe; R is a monoglysosyl of fructose or an oligosaccharyl of 2 fructose molecules linked together, in a structure of formula (II):

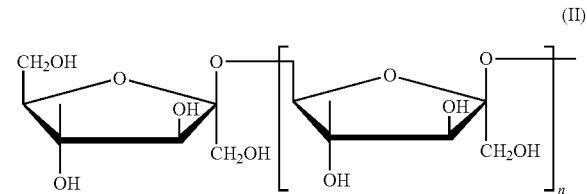

wherein n=0–1.

2. A method for preparing fructosylated mangiferin of claim 1, comprising (a) adding a substance having fructosylating enzymatic activity into a transformed liquid containing mangiferin; (b) performing a biotransformation reaction to convert said mangiferin into a fructosylated mangiferin; (c) after completion of said biotransformation reaction, removing bacteria cells or bacteria protein from said transformed liquid; and (d) purifying said transformed liquid with resin, which is then dried by rotary evaporation or freezing to obtain fructosylated mangiferin powder or crystal.

3. The method of claim 2, wherein said transformed liquid contains the mangiferin and a glycosyl donor.

4. The method of claim 3, wherein said glycosyl donor is fructose or cane sugar.

5. The method of claim 2, wherein said substance having fructosylating enzyme activity is fermentation liquor with fructosylating enzyme activity, fermentation liquor supernatant, purified fructosylating enzyme or recombinant fructosylating enzyme.

6. The method of claim 5, wherein said fructosylating enzyme is beta-D-fructofuranosidase.

7. The method of claims 2, wherein said fermentation liquor or fermentation liquor supernatant is obtained from fermentation by a microorganism with fructosylating enzyme activity.

8. The method of claims 7, wherein said microorganism is *Arthrobacter nicotianae* XM6 and fermentation is conducted with a fermentation medium containing cane sugar of 5~80 g/L, peptone of 5~50 g/L, $KH_2PO_4$ 0.4~4 g/L, $CaCl_2$ 0.5~5 g/L, $MnSO_4$ 0.1~2 g/L, pH 6~8, in a shake flask at 25~40° C., and oscillating at 10~400 rpm, or in a fermenting tank for agitating with ventilation, at a speed and ventilatory capacity of 1~6 vvm, 10~400 rpm, to ferment for 6~48 hours.

9. The method of claims 2, where said biotransformation reaction is conducted in a nonaqueous reaction condition which comprises oscillating in a shake flask at 10~400 rpm or agitating in a fermenting tank, in 5~50% hydrophilic organic solvent, with a mangiferin concentration of 0.1~70 g/L and a mangiferin to glycosyl donor mole ratio of 1:1~1:200, and using 10%~50% fermentation liquor or fermentation liquor supernatant, which contains fructosylated enzyme 10~100 U/mL, and said nonaqueous reaction lasts 6~400 hours at 25~40° C., in a buffer solution of pH4~8.

10. The method of claim 9, wherein said hydrophilic organic solvent is one or several selected from the group consisting of dimentyl sulfoxide, dimentyl formamide, acetonitrile, methanol, acetone or ethanol, and said nonaqueous phase reaction condition comprises a solution with 20% of DMSO, 62.7 g/L of mangiferin and 200 g/L of cane sugar as glycosyl donor, 20% of fermentation liquor supernatant containing fructosylating enzyme at 30 U/mL, in a 5 L fermenting tank containing phosphate buffer at 1/15 mol/L and pH6.86, for transformation with agitation at 300 rpm at 30° C. for 360 hours.

11. The method of claim 2, wherein said resin purification in step(d) is a process of passing said transformed liquid containing fructosylated mangiferin through AB-8 macroporous resin for adsorption and, after the adsorption, washing off remaining glycosyl donor with an eluant, which is then followed by gradient or stage elution with the eluant, to obtain purified fructosylated mangiferin.

12. The method of claim 11, wherein said adsorption is conducted under a condition under which said organic solvent in said transformed liquid has been removed by evaporation at low temperature or has been diluted to less than 2% volumetric ratio.

13. A method of treating a tumor disease by administering to a mammal in need of such treatment with a pharmaceutically effective amount of fructosylated mangiferin of claim 1.

14. The method of claim 13, wherein said mammal is human.

\* \* \* \* \*